United States Patent [19]

Molines et al.

[11] Patent Number: 4,992,592
[45] Date of Patent: Feb. 12, 1991

[54] 1-FLUORO-1-HALO-3,6-DIOXABICYCLO [4.1.0]HEPTANE PREPARATION, PROCESS AND USE

[75] Inventors: Huguette Molines; Claude Wakselman, both of Paris, France

[73] Assignee: Rhone-Poulenc Chimie, Courbevoie Cedex, France

[21] Appl. No.: 351,272

[22] Filed: May 11, 1989

Related U.S. Application Data

[62] Division of Ser. No. 191,047, May 6, 1988, abandoned.

[30] Foreign Application Priority Data

May 6, 1987 [FR] France ................................ 87 06600

[51] Int. Cl.$^5$ ............................................. C07C 41/50
[52] U.S. Cl. ..................................... 568/603; 568/604
[58] Field of Search ........................ 568/603, 604, 592

[56] References Cited

PUBLICATIONS

Yamanaka et al., C.A., 42549b (1973).
Chemistry Lettters, 1981, pp. 107–110, Ishikawa and Takaoka.
Canadian Journal of Chemistry (1962), vol. 40, p. 1571, Buchanan, Dean and Pattison.
Journal Chemical Engineering Data, 1967, vol. 12, p. 452, Moss and Paige.

*Primary Examiner*—Howard T. Mars
*Attorney, Agent, or Firm*—Finnegan, Henderson, Farabow, Garrett, and Dunner

[57] ABSTRACT

A class of compounds, namely 1-fluoro-1-halo-3,6-dioxabicyclo[4.1.0]heptanes and a process using these compounds in the preparation of fluoromalonaldehyde acetals. The 1-fluoro-1-halo-3,6-dioxabicyclo[4.1.0]heptane is brought into contact with an alcohol in an acid medium. The fluoromalonaldehyde acetals obtained are also new products, which are useful for the synthesis of alkyl fluoromalonates or of fluorinated nitrogen-containing heterocycles.

6 Claims, No Drawings

1-FLUORO-1-HALO-3,6-DIOXABICYCLO[4.1.0]HEPTANE PREPARATION, PROCESS AND USE

This application is a division of application Ser. No. 07/191,047, filed May 6, 1988 now abandoned.

The present invention relates to a class of new products, 1-fluoro-1-halo-3,6-dioxabicycloheptanes and a process for preparing these compounds. It relates more specifically to the above class of compounds in which the halogen unit is chlorine or fluorine, and still more preferably to 1-chloro 1-fluoro-3,6-dioxabicyclo[4.1.0-]heptane. The present invention also relates to fluoromalonaldehyde acetal compounds and also to a process for making these compounds utilizing the 1-fluoro-1-halo-3,6-dioxabicycloheptanes of the invention. Finally, the present invention relates to a process for preparing fluoromalonates and also a process for preparing nitrogen-containing heterocycles utilizing the fluoromalonaldehyde acetals of the invention.

It is known, as disclosed by German Pat. No. 2,017,010, to prepare fluoromalonaldehyde having the formula:

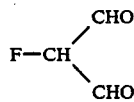

by alkali metal or alkaline earth metal hydrolysis of 2-fluoro-3-(dimethylamino)acrolein having the formula:

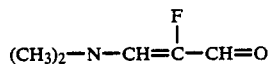

To prepare 2-fluoro-3-(dimethylamino)acrolein, sodium fluoroacetate is introduced into dimethylformamide, followed by addition of oxalyl chloride at a temperature below 10° C. The mixture is then heated to 60° C. After cooling to approximately 0° C., triethylamine is added slowly, maintaining a temperature below 10° C. The resulting operations of washing and extracting the acrolein are particularly difficult. This process is extremely lengthy and complicated and thus has hampered the industrial production of fluoromalonaldehyde.

The pharmaceutical industry has for a long time been seeking a simple and economic method for preparing fluoromalonates or their salts.

Ishikawa and Takaoka have proposed, in Chemistry Letters, 1981, pp. 107–110, a process for preparing such malonates from hexafluoropropene by alcoholysis. Fuchikami, Yamanouchi and Suzuki have described, in Chemistry Letters, 1984, pp. 1573–1576, a process for preparing such malonates from chlorotrifluoroethylene, proceeding via the lithium salt of trifluoroacrylic acid.

Since the starting materials used and the working conditions employed in these two processes are costly, such processes are not suitable for use at the industrial level.

The present invention enables fluoromalonates or their derivatives to be prepared by a new process, from more readily available starting materials. It enables, in addition, a class of new intermediates to be synthesized, namely 1-fluoro-1-halo-3,6-dioxabicyclo[4.1.0]heptanes of the following formula (I):

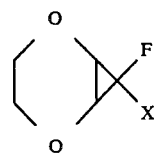

in which X denotes chlorine, bromine or fluorine.

The compounds of formula (I) in which X is chlorine or fluorine are preferred.

The process for preparing the fluoromalonates according to the present invention comprises, in a first stage, synthesizing the 1-fluoro-1-halo-3,6-dioxabicyclo[4.1.0]heptane, and in particular 1-chloro-1-fluoro-3,6-dioxabicyclo[4.1.0]heptane. To manufacture these intermediates, 1,4-dioxene or 1,4-dioxacyclohexene is brought into contact in a basic medium with a dihalofluoromethane of formula $HX_1FCX_2$, in which $X_1$ and $X_2$ denote a halogen which may be identical (except in the case of fluorine) or different and is chosen from among fluorine, chlorine or bromine, according to the following reaction:

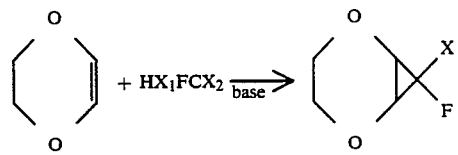

Among dihalofluoromethanes, it is preferred to use dichlorofluoromethane or chlorodifluoromethane.

This reaction is carried out in the presence of a base, preferably a strong inorganic base, optionally in aqueous solution, and, optionally, an organic solvent. The strong inorganic base may be selected from, for example, alkali metal or alkaline earth metal hydroxides. If an organic solvent is used, a solvent should be selected that does not participate in the reaction. Among the solvents that may be used are, for example, halomethanes such as dichloromethane, and aromatic hydrocarbons such as benzene or toluene. When the reaction is carried out in the presence of a base that is not soluble in the organic medium, a phase transfer agent is added to the mixture. The phase transfer agent may be selected, for example, from ammonium or phosphonium salts, or from tertiary amines. Representative tertiary amines include, in particular, tris(polyoxaalkyl)amines and, more particularly, tris(dioxaheptyl)amine.

The reaction temperature conditions are preferably not too severe. A temperature of between 0° and 20° C. is preferred. Pressure above atmospheric is not necessary for the reaction to take place, however, since dihalofluoromethanes are gaseous, a pressure of between 1 and 5 bars is preferred.

After the reaction is complete, the 1-fluoro-1-halo-3,6dioxabicyclo[4.1.0]heptane is, depending on the reaction conditions, either filtered or extracted with a suitable organic solvent selected from among, for example, ethers, halomethanes or hydrocarbons.

The process for preparing fluoromalonaldehyde acetals according to the present invention takes place in a second stage, bringing the previously synthesized 1-fluoro-1-halo-3,6-dioxabicyclo[4.1.0]heptane into contact with a strong acid and an alcohol having the formula ROH according to the following reaction:

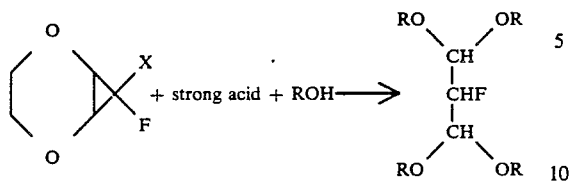

The alcohol of formula ROH is preferably selected from among, for example, aliphatic alcohols preferably containing 1 to 8 carbon atoms, and more preferably is methanol or ethanol. The aliphatic alcohols can be unsubstituted or substituted, for example, by an aromatic group.

The strong acid is selected from among, for example, sulfuric acid, trifluoroacetic acid, trifluoromethanesulfonic acid and hydrochloric acid.

The reaction conditions involved in this second stage will be selected by one skilled in the art in accordance with the reactivity of the acid and the rate of the reaction. It is preferred to utilize a temperature ranging from 40° to 200° C., and when utilizing methanol or ethanol as the alcohol, a temperature ranging from 45° to 120° C. is preferred.

The present invention thus also relates to production of fluoromalonaldehyde acetals having the following formula (II):

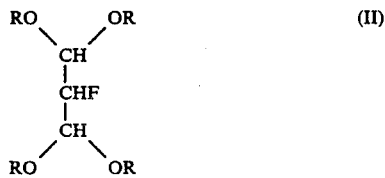

in which R represents an alkyl group containing 1 to 8 carbon atoms.

The present invention also relates to a process for the production of alkyl fluoromalonates. Fluoromalonaldehyde acetals may be readily oxidized to alkyl fluoromalonates according to methods known to those skilled in the art. Among the oxidizing agents that may be used are, for example, an inorganic peracid, such as Caro's acid, consisting of a mixture of ammonium persulfate and 90% sulfuric acid, or an organic peracid such as peracetic acid.

The present invention also relates to the production of nitrogen-containing heterocycles. The fluoromalonaldehyde acetals of the present invention may be contacted with hydrazinium dichloride, water and ethanol to form nitrogen-containing heterocyclic compounds that are fluorinated on the ring, such as 4-fluoropyrazoles and fluoropyrimidines.

Fluoromalonaldehyde is useful, for example, as described in German Pat. No. 2,016,990, for the preparation of nitrogen-containing heterocycles substituted with a fluorine atom which possess anticancer, antineoplastic and antibacterial properties. Alkyl fluoromalonates are useful in the synthesis of amino acids and of fluorinated heterocycles such as, for example, fluorouracil, which is an antineoplastic. As disclosed by Fuchikami, Yamanouchi and Suzuki in Chemical Letters (1984), pp. 1573–1576, fluoromalonic acid diesters are useful for preparing fluorouracil. According to Buchanan, Dean and Pattison, Canadian Journal of Chemistry (1962), Vol. 40, p. 1571, fluoromalonic acid diesters can be used to prepare alpha-fluoroglutamic acid.

The present invention will be described more completely by means of the examples which follow, which must not be considered to limit the invention.

Example 1 is directed to the preparation of 1,4-dioxene.

EXAMPLE 1

1,4-dioxene was prepared according to the paper by R. P. Moos and J. Paige in J. Chem. Eng. Data, 1967, Vol. 12, p. 452.

Examples 2–4 are directed to the preparation of 1-chloro-1-fluoro-3,6-dioxabicyclo[4.1.0]heptane.

EXAMPLE 2

Dichlorofluoromethane (23.7 g; 0.23 mol; 1.5 equivalents) was bubbled through a mixture of 1,4-dioxene (12.9 g; 0.15 mol; 1 equivalent), dichloromethane (15 ml), aqueous sodium hydroxide at a concentration of 50% by weight (45 ml) and benzyltriethylammonium chloride (TEBA; 0.05 g). The mixture was stirred vigorously and the temperature maintained at between 5° and 10° C. After the addition of $CHFCl_2$, the reaction mixture was stirred for 14 hours at 20° C., and water (300 ml) was then added. The products were extracted with dichloromethane (3×200 ml). The organic phase was washed with saturated sodium chloride solution and dried (sodium sulfate). The solvents were evaporated (20 mm Hg). The residue consisted of a mixture of the two isomers, cis and trans (58% - 42%), of the pure 1-chloro-1-fluoro-3,6 dioxabicyclo[4.1.0]heptane (20.8 g; 0.1365 mol; 91% yield)

B.p. 75°–76° C./18 mm Hg.

1H NMR ($CDCl_3$, TMS): =3.6–4.1 ppm (m, 4 broad lines). 19F NMR ($CDCl_3$, $CFCL_3$): =−145 ppm (cis isomer, t, 3 JFH=14 Hz) - 170 ppm (trans isomer, s).

Analysis: calculated for $C_5H_6ClFO_2$ (152.55): C, 39.36%; H, 3.96%; found: C, 39.76%; H, 4.06%.

EXAMPLE 3

1,4-dioxene was prepared as in Example 1. $CHFCl_2$ (16.5 g; 0.16 mol; 2 eq.) was bubbled through a vigorously stirred mixture of 1,4-dioxene (6.9 g; 0.08 mol; 1 equivalent), tris (dioxaheptyl) amine (1-TDA) (1.28 g; 4×10$^{-3}$ mol) and finely powdered NaOH (8 g; 0.2 mol; 2.5 eq.); the temperature was maintained at between 5° and 10° C. The mixture was then stirred for 14 hours at room temperature, after which it was filtered; the gummy solid was rinsed with dichloromethane (3×10 ml). The combined organic phases were evaporated (20 mm Hg). The residue was a mixture of 1,4-dioxene and 1-chloro-1-fluoro-3,6 dioxabicyclo[4.1.0]heptane, which were separated by distillation. 3.8 g (0.025 mol; 31% yield) of 1-chloro-1-fluoro 3,6-dioxabicyclo[4.1.0-]heptane were obtained.

EXAMPLE 4

The procedure was the same as for Example 2, with 0.1 mol of 1,4-dioxene dissolved in $CH_2Cl_2$ (50 ml). 5.5 g (0.036 mol; 36% yield) of 1-chloro-1-fluoro-3,6 dioxabicyclo[4.1.0]heptane were obtained after distillation.

Examples 5–8 are directed to the production of fluoromalonaldehyde bis(diethyl acetal).

EXAMPLE 5

A mixture of, 1-chloro-1-fluoro-3,6 dioxabicyclo[4.1.0]heptane (6.1 g; 0.04 mol), absolute ethanol (40 ml) and concentrated sulfuric acid (0.2 ml) was heated to reflux for 6 days and then cooled and poured into ice-cold water (50 ml). The products were extracted with ethyl ether (3×50 ml). The organic phase was neutralized with saturated sodium bicarbonate solution, washed with saturated sodium chloride solution and then dried over sodium sulfate. The solvents were evaporated (20 mm Hg) and the residue was distilled to give fluoromalonaldehyde bis(diethyl acetal) (7.6 g; 0.032 mol; 80% yield).

B.p. 118°–125° C./12 mm Hg

1H NMR (CDCl$_3$, TMS): =1.25 (t, 12 H, 3JHH =7Hz); 3.7–4.7 ppm (11H).

19F NMR (CDCl$_3$, CFCl$_3$): = −214 ppm (m); −211 ppm (m).

Analysis: calculated for $C_{11}H_{23}FO_4$ (238.3): C, 55.44%; H, 9.73%; found: C, 55.46%; H, 9.82%.

EXAMPLE 6

The procedure was the same as for Example 4 with the exception that concentrated sulfuric acid was replaced by trifluoroacetic acid. 1.8 g (7.5×10$^{-3}$ mol) of fluoromalonaldehyde bis(diethyl acetal) were obtained from 1.52 g (0.01 mol) of 1-chloro-1-fluoro-3,6 dioxabicyclo[4.1.0]heptane.

EXAMPLE 7

The procedure was the same as for Example 4, concentrated sulfuric acid being replaced by trifluoromethanesulfonic acid. 1.9 g (7.9×10$^{-3}$ mol) of fluoromalonaldehyde bis(diethyl acetal) were obtained from 1.52 g (0.01 mol) of 1-chloro-1-fluoro-3,6 dioxabicyclo[4.1.0]heptane.

EXAMPLE 8

A mixture of 1-chloro-1-fluoro-3,6 dioxabicyclo[4.1.0]heptane (4.6 g; 0.03 mol), absolute ethanol (45 ml) and concentrated sulfuric acid (0.1 ml) was placed in a 125 ml autoclave, and the mixture was then heated for 6 hours to 120° C. After cooling, the treatment of the reaction mixture was identical to that described in Example 4. 3.4 g (0.01428 mol; 47.6% yield) of fluoromalonaldehyde bis(diethyl acetal) were obtained.

Example 9 is directed to the production of fluoromalonaldehyde bis(dimethyl acetal).

EXAMPLE 9

A mixture of 1-chloro-1-fluoro-3,6 dioxabicyclo[4.1.0]heptane (3.5 g; 0.0229 mol), methanol (30 ml) and trifluoroacetic acid (0.1 ml) was placed in a 125 ml autoclave, and the mixture was heated to 120° C. for 6 hours. After cooling, the treatment of the reaction mixture was identical to that described in Example 4. After evaporation of the solvents (20 mm Hg), distillation of the residue gave fluoromalonaldehyde bis(dimethyl acetal) (1.7 g; 9.34×10$^{-3}$ mol; 41% yield).

B.p. 86°–88° C./17 mm Hg.

1H NMR (CDCl$_3$, CFCl$_3$): =3.5 (s, 12H); 4.3–4.8 ppm (m, 3H).

19F NMR (CDCl$_3$, CFCl$_3$): = −210 ppm (m); −213 ppm (m).

Analysis: calculated for $C_7H_{15}FO_4$ (182.194): C, 46.15%; H, 8.30%; found: C, 46.25%; H, 8.17%.

Examples 10 and 11 are directed to the production of ethyl fluoromalonate.

EXAMPLE 10

Caro's acid [0.15 mol; 5 equivalents; prepared from ammonium persulfate (34.2 g; 0.15 mol) and 90% sulfuric acid (42 g)] was added to a solution of fluoromalonaldehyde bis(diethyl acetal) (7.14 g; 0.03 mol) in absolute ethanol (60 ml). The temperature was maintained below 10° C. during the addition. The mixture was then stirred vigorously for 18 hours at room temperature; water (200 ml) was then added and the products were extracted with ethyl ether (3×200 ml). The organic phase was washed with saturated sodium chloride solution and then dried (sodium sulfate). The solvents were evaporated (20/mm Hg). Distillation of the residue gave ethyl fluoromalonate (2.9 g; 0.0163 mol; 54% yield).

B.p. 90°–95° C./12 mm Hg [literature: 110°–111° C./20 mm Hg (N. Ishikawa, A. Takaoka, Chem. Letters 1981, p. 107)].

EXAMPLE 11

A mixture of 1-chloro-1-fluoro-3,6 dioxabicyclo[4.1.0]heptane (6.1 g; 0.04 mol), absolute ethanol (40 ml) and concentrated sulfuric acid (0.15 ml) was heated to reflux for 5 days, and then cooled to 0° C. Caro's acid [0.2 mol; 5 equivalents; prepared from ammonium persulfate (46.5 g; 0.2 mol) and 90% sulfuric acid (56 g)] was added. The temperature was maintained below 10° C. during the addition. The mixture was then stirred vigorously for 18 hours at 20° C., after which it was treated as in Example 9. 3.1 g (0.0174 mol; yield: 43.5%) of ethyl fluoromalonate were obtained.

Example 12 is directed to the condensation of fluoromalonaldehyde bis(diethyl acetal) with hydrazine for the production of 4-fluoropyrazole.

EXAMPLE 12

A mixture of fluoromalonaldehyde bis(diethyl acetal) (1.2 g; 0.005 mol), hydrazinium dichloride (0.525 g; 0.005 mol), water (0.75 ml) and ethanol (0.5 ml) was heated to reflux for two hours. After cooling, the mixture was filtered and water (1 ml) and disodium carbonate (1 g) were then added to the filtrate. This new mixture was filtered. The organic products were extracted from the filtrate with ethyl ether (2×5 ml); the organic phase was washed with saturated sodium chloride solution (2×5 ml) and then dried (sodium sulfate). The solvents were evaporated (20 mm Hg). The residue was 4-fluoropyrazole (0.35 g; 0.004 mol).

What is claimed is:

1. A process for preparing a fluoromalonaldehyde acetal comprising contacting a 1-fluoro-1-halo-3,6-dioxabicyclo heptane compound of the formula (I):

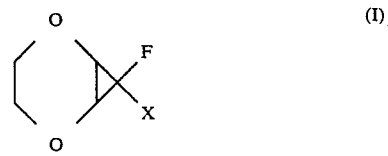

wherein X is selected from the group consisting of fluorine, chlorine and bromine, in a reaction mixture with a strong acid and an alcohol for a time sufficient to cause the formation of said fluoromalonaldehyde acetal.

2. The process of claim 1, wherein said alcohol is aliphatic containing 1 to 8 carbon atoms.

3. The process of claim 2, wherein said alcohol is selected from methanol and ethanol.

4. The process of claim 1, wherein said strong acid is selected from sulfuric acid, hydrochloric acid, trifluoroacetic acid and trifluoromethanesulfonic acid.

5. The process of claim 1, wherein the reaction is conducted at a temperature ranging from 40° C. to 200° C.

6. The process of claim 3, wherein the reaction is conducted at a temperature ranging from 45° C. to 120° C.

* * * * *